United States Patent

Takahara et al.

Patent Number: 4,542,209
Date of Patent: Sep. 17, 1985

[54] FLUORINE-CONTAINING URIDINE DERIVATIVE AND PREPARATION AND USE THEREOF

[75] Inventors: Takao Takahara; Yorisato Hisanaga, both of Osaka, Japan

[73] Assignee: Daikin Kogyo Co., Ltd., Osaka, Japan

[21] Appl. No.: 558,913

[22] Filed: Dec. 7, 1983

[30] Foreign Application Priority Data

Dec. 9, 1982 [JP] Japan .................. 57-215748
Dec. 9, 1982 [JP] Japan .................. 57-215749

[51] Int. Cl.⁴ ............................ C07H 19/06
[52] U.S. Cl. ........................ 536/23; 536/122
[58] Field of Search .................. 536/23, 122

[56] References Cited

U.S. PATENT DOCUMENTS 3,928,319 12/1975 Jenkins et al. ............ 536/23
4,122,251 10/1978 Misaki et al. ............ 536/23
4,122,252 10/1978 D'Souza et al. .......... 536/23

Primary Examiner—Johnnie R. Brown
Attorney, Agent, or Firm—Birch, Stewart, Kolasch & Birch

[57] ABSTRACT

A fluorine-containing uridine derivative of the formula:

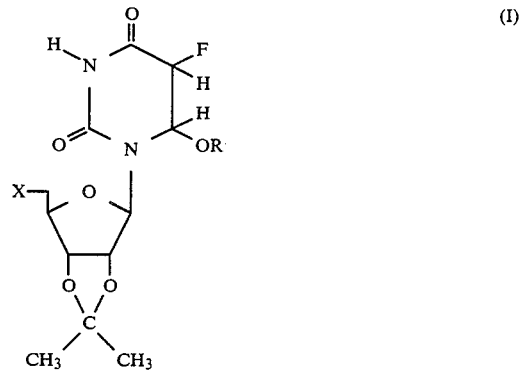

wherein R is lower acyl, fluorine-containing lower acyl or fluorine-containing lower alkyl; and X is hydrogen or hydroxyl, which is prepared by a process which comprises fluorinating 2', 3'-O-isopropylideneuridine with fluorine in a solvent selected from the group consisting of lower carboxylic acids, fluorine-containing lower carboxylic acids and fluorine-containing lower alcohols, and is converted to a 5-fluorouridine derivative of the formula:

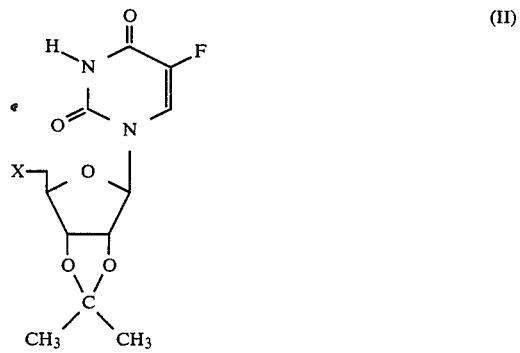

wherein R and X are as defined above by reacting the fluorine-containing uridine derivative of the formula (I) with a base in an organic solvent at a temperature of 0° to 80° C.

20 Claims, No Drawings

FLUORINE-CONTAINING URIDINE DERIVATIVE AND PREPARATION AND USE THEREOF

FIELD OF THE INVENTION

The present invention relates to a novel fluorine-containing uridine derivative and preparation and use thereof. More particularly, it relates to a novel fluorine-containing uridine derivative which is useful as an intermediate in the preparation of 5-fluorouridine which is a carcinostatic or antitumor substance, a process for preparing the novel fluorine-containing uridine derivative comprising fluorinating 2',3'-O-isopropylideneuridine with fluorine, and a process for preparing 5-fluorouridine and its derivatives from the novel fluorine-containing uridine derivative by reacting it with a base.

BACKGROUND OF THE INVENTION

Among known fluorine-containing nucleic acid-relating substances, 5-fluorouracil and 5-fluorouridine are well known carcinostatic or antitumor substances.

Derivatives of 5-flourouracil such as the compounds of the formulas:

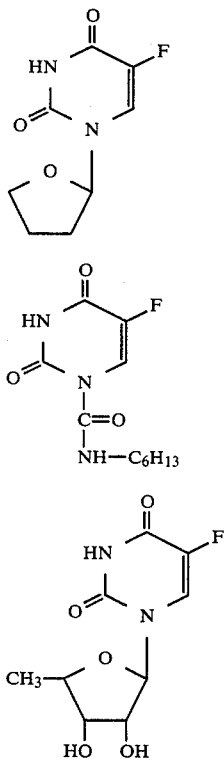

are widely used as carcinostatic or antitumor substances which can suppress side effects of 5-fluorouracil. One of the known processes for preparing these 5-flourouracil derivatives comprises adding a glycoresidue to 5-fluorouracil. According to this process, expensive 5-fluorouracil is not effectively utilized, and this makes the conventional production of the 5-fluorouracil derivatives commercially disadvantageous.

Another known process for preparing 5-Fluorouracil derivatives comprises dehydrating 5,6-dihydro-5-fluoro-6-hydroxyuridine, which has been prepared by reacting uridine with fluorine in water, at a high temperature in the presence of a strong acid such as hydrochloric acid (cf. Japanese Patent Publication (unexamined) No. 28926/1980). According to this process, the obtained product is hardly crystallized probably due to the presence of by-products and it is difficult to improve the purity of the product only by crystallization. Therefore, it must be purified by the use of silica gel and/or cation exchange resin, which is commercially disadvantageous.

SUMMARY OF THE INVENTION

The present invention provides a novel fluorine-containing uridine derivative of the formula:

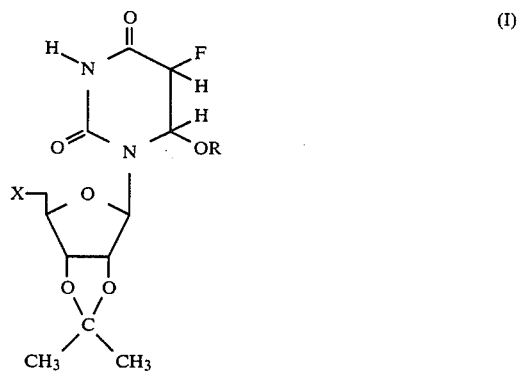

wherein R is lower acyl, fluorine-containing lower acyl or fluorine-containing lower alkyl; and X is hydrogen or hydroxyl.

In the specification, lower acyl and alkyl are intended to include those having 1 to 10 carbon atms, preferably 1 to 5 carbon atoms, for example, formyl, acetyl, propanoyl, butanoyl, pentanoyl, methyl, ethyl, propyl, butyl and pentyl.

According to the invention, the fluorine-containing uridine derivative of the formula (I) is prepared by fluorinating 2',3'-O-isopropylideneuridine with fluorine in a solvent selected from the group consisting of lower carboxylic acids, fluorine-containing lower carboxylic acids and fluorine-containing lower alcohols.

The present invention further provides a process for preparing a 5-fluorouridine derivative of the formula:

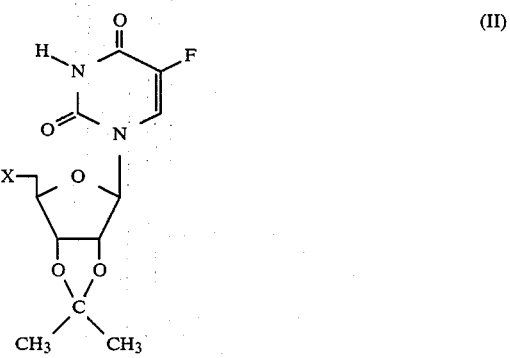

wherein X is as defined above comprising reacting the fluorine-containing uridine derivative of the formula (I) with a base in an organic solvent at a temperature of 0° to 80° C.

DETAILED DESCRIPTION OF THE INVENTION

The novel fluorine-containing uridine derivative of the formula (I) has a pyrimidine ring in which at the 5-position, fluorine is added and at the 6-position, a group —OR wherein R is as defined above is added as follows:

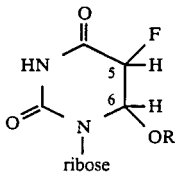 (III)

wherein R is as defined above. Therefore, the fluorine-containing uridine derivative of the formula (I) mainly comprises two isomers of the formula:

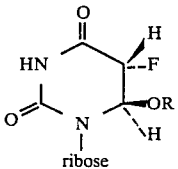 (IVa)

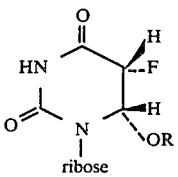 (IVb)

wherein R is as defined above.

2',3'-O-Isopropylideneuridine to be fluorinated according to the invention is a compound of the formula:

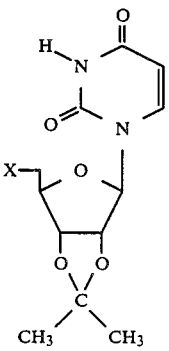 (V)

wherein X is as defined above. Uridine of the formula (V) is, for example, prepared by reacting a uridine compound of the formula:

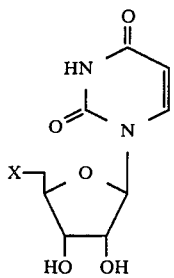 (VI)

wherein X is as defined above with 2,2-dimethoxypropane in acetone in the presence of para-toluenesulfonic acid monohydrate as a catalyst for several hour at 20° C. (cf. Tetrahedron, 23, 2323 (1967)).

Fluorine to be used in the process of the invention is usually fluorine gas diluted with an inert gas such as nitrogen and helium in a concentration of not more than 50% by mole, preferably 10 to 20% by mole, although pure fluorine gas may be used.

The solvent to be used as the reaction medium according to the invention is one selected from the group consisting of lower carboxylic acids, fluorine-containing lower carboxylic acids and fluorine-containing lower alcohols. Specific examples of the solvent are acetic acid, propionic acid and butyric acid and fluorinated derivatives thereof and a fluorinated alcohol of the formula:

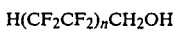

$H(CF_2CF_2)_nCH_2OH$ wherein n is an integer of 1 to 5.

The reaction temperature is usually from 0 to 50° C., preferably from 5° to 20° C.

The fluorine-containing uridine derivative of the formula (I) is recovered from the reaction mixture by a per se conventional method, for example, by precipitation, crystallization or evaporation of the solvent and purified by a per se conventional method, for example, by recrystallization, although it may be used without isolation in a subsequent reaction to obtain 5-fluorouridine derivative of the formula (II).

According to the invention, 5-fluorouridine derivative of the formula (II) is prepared by reacting the fluorine-containing uridine derivative of the formula (I) with the base in an organic solvent at a temperature of from 0° to 80° C.

Specific examples of the base to be used are organic base such as triethylamine, diethylamine, pyridine, picoline, etc. and inorganic base such as ammonia, sodium bicarbonate, etc. Among them, amines are preferred.

The organic solvent may be a mixture of esters of lower carboxylic acids (eg. ethyl acetate), acetone, acetonitrile or dioxane and not more than 50% by volume of a lower alcohol (eg. methanol, ethanol, etc.). A mixture of ethyl acetate and 10% by volume of methanol is preferred.

The reaction temperature is from 0° to 80° C., preferably from 10° to 30° C. The reaction time is usually from 5 to 24 hours.

The 5-Fluorouridine derivative of the formula (II) is easily crystallized from its solution in a solvent such as lower alcohols (eg. methanol, ethanol, etc.).

PREFERRED EMBODIMENTS OF THE INVENTION

The present invention will be hereinafter explained further in detail by following Examples.

EXAMPLE 1

A solution of 2',3'-O-isopropylideneuridine (2.84 g, 10.0 mmol) in glacial acetic acid (100 ml) was bubbled with nitrogen gas containing 10% by mol of fluorine gas at a rate of 60 ml/min. for one hour (fluorine; 12 mmol.) at a temperature of 13° to 18° C. while stirring the mixture vigorously. After the fluorination, glacial acetic acid was evaporated off, and the residue was recrystallized from methanol to obtain an isomeric mixture (3 g, 8.29 mmol. Yield, 82.9%) of the fluorinated uridine derivatives of the formulas:

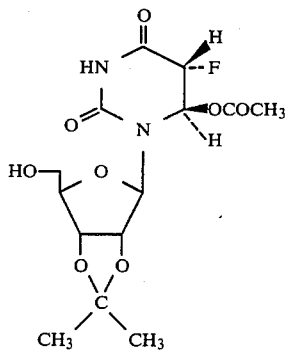

(Ia)

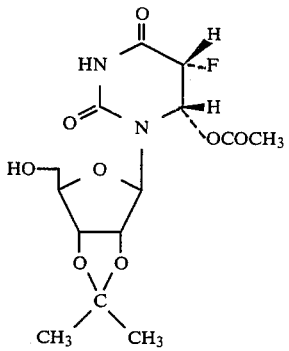

(Ib)

| | Elementary Analysis | | | |
|---|---|---|---|---|
| | C | H | N | F |
| Found: | 47.0%; | 5.3%; | 8.0%; | 5.7% |
| Calc'd: | 46.4%; | 5.2%; | 7.7%; | 5.2% |

UV absorption

UV absorption appeared at 250–270 cm$^{-2}$ in the starting material, 2',3'-O-isopropylideneuridine was disappeared in the reaction product.

$^{19}$F-NMR (external standard; CF$_3$COOH)

Compound (Ia): δ (ppm)=131.0 (d×d, $J_{F5H5}$=50 Hz, $J_{F5H6}$=8 Hz).

Compound (Ib): δ (ppm)=133.0 (d×d, $J_{F5H5}$=51 Hz, $J_{F5H6}$=8 Hz).

$^1$H-NMR

δ (ppm)=5.00–5.50 (combined peak), 2.15 (acetyl, —CH$_3$), 1.33 and 1.48 (isopropylidene, —CH$_3$).

From the results of $^{19}$F-NMR, the proportion of the Compounds (Ia) and (Ib) was about 1:1.

EXAMPLE 2

In the same manner as in Example 1, but using 5'-deoxy-2',3'-O-isopropylideneuridine in place of 2',3'-O-isopropylideneuridine, the reaction was carried out to obtain an isomeric mixture (2.78 g, 8.01 mmol. Yield, 80.1%) of the compounds of the formulas:

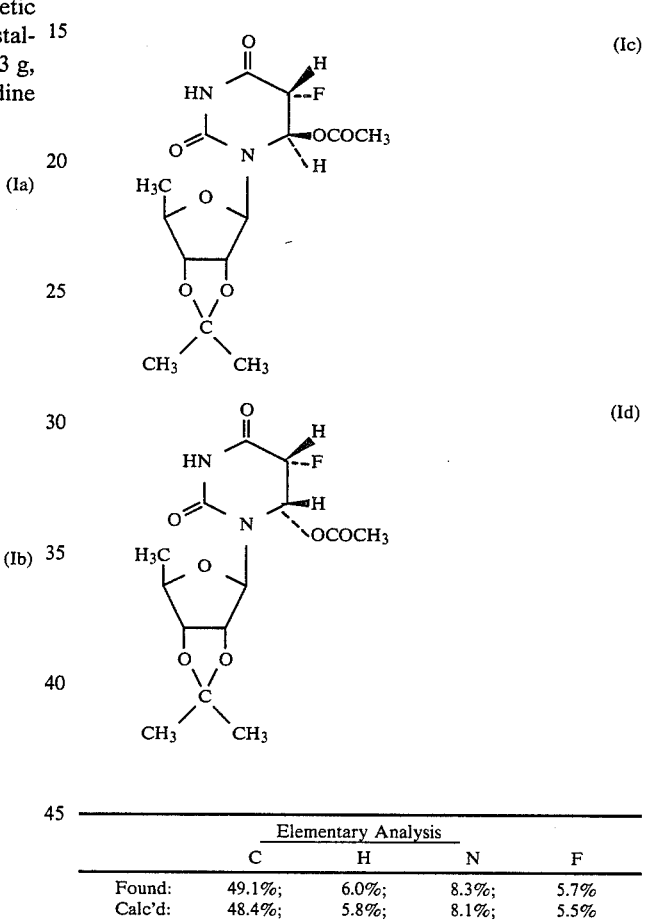

| | Elementary Analysis | | | |
|---|---|---|---|---|
| | C | H | N | F |
| Found: | 49.1%; | 6.0%; | 8.3%; | 5.7% |
| Calc'd: | 48.4%; | 5.8%; | 8.1%; | 5.5% |

UV absorption

UV absorption appeared at 250–270 cm$^{-2}$ in the starting material, 5'-deoxy-2',3'-O-isopropylideneuridine was disappeared in the reaction product.

$^{19}$F-NMR

Same as those of the product of Example 1.

$^1$H-NMR

δ (ppm)=1.30 and 1.4 (isopropylidene, —CH$_3$) and 1.40 (d, J=7 Hz, —CH$_3$ at 4'-position).

EXAMPLE 3

The fluorine-containing uridine derivative obtained in Example 1 (3 g, 8.29 mmole) was dissolved in a mixture (60 ml) of triethylamine, methanol and ethyl acetate in a volume ratio of 3:4:20 and reacted at 20° C.

with stirring for 12 hours. After the reaction, the reaction mixture was evaporated under a reduced pressure. The residue was recrystallized from methanol to obtain a white needle-like crystalline compound (1.78 g, 5.88 mmol). Yield, 70.9%) of the formula:

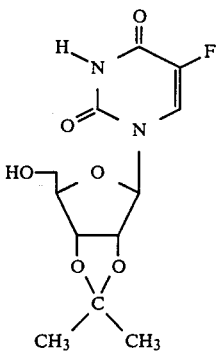

Melting point, 198.5°–199.5° C.

$^{19}$F-NMR

δ (ppm)=89.0 (d×d, $J_{F5H6}$=8 Hz, $J_{F5H1'}$=2 Hz).

$^1$H-NMR

δ (ppm)=1.32 and 1.51 (3H, s, isopropylidene, —C$\underline{H}_3$), 3.68 (2H, d, H$_5'$, J=5 Hz), 4.18 (1H, q, H$_2'$, J=3 Hz), 4.96 (1H, q, H$_3'$, J=3 Hz), 5.86–5.94 (1H, m, H$_1'$) and 8.20 (1H, d, H$_6$, J=7 Hz).

EXAMPLE 4

In the same manner as in Example 3 but using the fluorine-containing uridine derivative obtained in Example 2 (2.78 g, 8.01 mmol) in place of the fluorine-containing uridine derivative obtained in Example 1, the reaction was carried out to obtain a white needle-like compound (1.77 g, 6.18 mmol. Yield, 77.1%) of the formula:

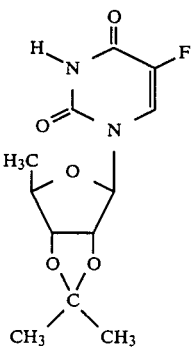

Melting point, 196°–197° C.

$^{19}$F-NMR

Same as that of the product of Example 3.

$^1$H-NMR

δ (ppm)=1.30 and 1.57 (3H, s, isopropylidene, —C$\underline{H}_3$) and 8.12 (H$_6$).

REFERENCE EXAMPLE

The 5-Fluorouridine derivative obtained in Example 4 (1.77 g, 6.18 mmol) was dissolved in a 90% by weight aqueous solution of CF$_3$COOH (10 ml) and reacted at a room temperature for 1 hour with stirring. After the reaction, the reaction mixture was evaporated under a reduced pressure. The residue was recrystallized from methanol to obtain white crystalline 5'-deoxy-5-fluorouridine (1.40 g, 5.69 mmol. Yield, 92.1%) of the formula:

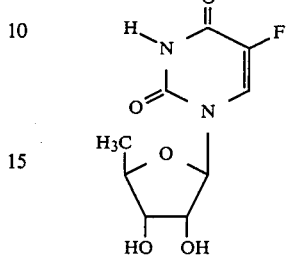

Melting point, 186°–188° C.

$^{19}$F-NMR

Same as that of the product of Example 3.

$^1$H-NMR

δ (ppm)=7.88 (1H, d, J=7 Hz, C$\underline{H}$CF) and 5.3 (2H, m, OH).

COMPARATIVE EXAMPLE 1

A fluorine-containing uridine (3 g, 8.64 mmol) of the formula:

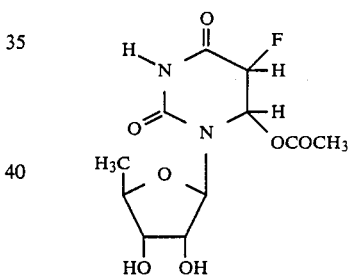

was dissolved in a mixture (60 ml) of triethylamine, methanol and ethyl acetate in a volume ratio of 3:4:20 and reacted at 20° C. for 12 hours with stirring. After the reaction, the reaction mixture was evaporated under a reduced pressure. The residue could not crystallize from methanol.

COMPARATIVE EXAMPLE 2

To a solution of fluorine-containing uridine (3 g, 10.7 mmol) of the formula:

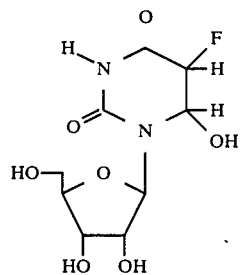

in water (10 ml), concentrated hydrochloric acid (10 ml) was added and reacted at 80° C. for 30 minutes under stirring. The reaction mixture was evaporated. The residue could not crystallize from methanol.

What is claimed is:

1. A fluorine-containing uridine derivative of the formula:

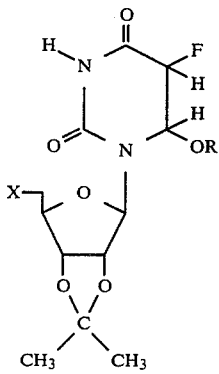

(I)

wherein R is lower acyl, fluorine-containing lower acyl or fluorine-containing lower alkyl; and X is hydrogen or hydroxyl.

2. A fluorine-containing uridine derivative according to claim 1, wherein R is lower acyl.

3. A fluorine-containing uridine derivative according to claim 1, wherein R is fluorinated lower acyl.

4. A fluorine-containing uridine derivative according to claim 1, wherein R is fluorinated lower alkyl.

5. A fluorine-containing uridine derivative according to claim 1, wherein X is hydrogen.

6. A fluorine-containing uridine derivative according to claim 1, wherein X is hydroxy.

7. A fluorine-containing uridine derivative according to claim 1, wherein R is acetyl and X is hydroxy.

8. A fluorine-containing uridine derivative according to claim 1, wherein R is acetyl and X is hydrogen.

9. A process for preparing a fluorine-containing uridine derivative of the formula (I) as defined in claim 1, comprising fluorinating 2′,3′-O-isopropylideneuridine with fluorine in a solvent selected from the group consisting of lower carboxylic acids, fluorine-containing lower carboxylic acids and fluorine-containing lower alcohols.

10. A process according to claim 9, wherein fluorination is effected at a temperature of 0° to 50° C.

11. A process according to claim 9, wherein fluorination is effected in the presence of a fluorination agent which comprises fluorine gas diluted with an inert gas.

12. A process according to claim 9, wherein the solvent is a lower carboxylic acid selected from the group consisting of acetic acid, propionic acid and butyric acid.

13. A process according to claim 9, wherein the solvent is a fluorine-containing lower carboxylic acid selected from the group consisting of fluorinated acetic acid, fluorinated propionic acid and fluorinated butyric acid.

14. A process according to claim 9, wherein the solvent is a fluorine-containing alcohol of the formula:

$$H(CF_2CF_2)_nCH_2OH$$

wherein n is an integer of 1 to 5.

15. A process for preparing a 5-fluorouridine derivative of the formula:

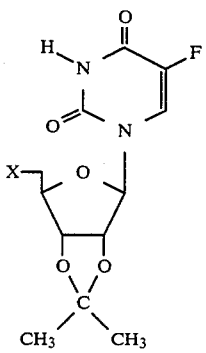

(II)

wherein R is lower acyl, fluorine-containing lower acyl or fluorine-containing lower alkyl; and X is hydrogen or hydroxyl comprising reacting the fluorine-containing uridine derivative of the formula (I) as defined in claim 1 with a base in an organic solvent at a temperature of 0° to 80° C.

16. A process according to claim 15, wherein the base is one selected from the group consisting of triethylamine, diethylamine, pyridine, picoline, ammonia and sodium bicarbonate.

17. A process according to claim 16, wherein the solvent is a mixture of an ester of a lower carboxylic acid, acetone, acetonitrile or dioxane and not more than 50% by volume of a lower alcohol.

18. A process according to claim 16, wherein the reaction temperature is 0° to 80° C.

19. A process according to claim 9, wherein fluorination is effected at a temperature of 5° to 20° C.

20. A process according to claim 16, wherein the reaction temperature is 10° to 30° C.

* * * * *